United States Patent
Istoc

(10) Patent No.: US 8,487,758 B2
(45) Date of Patent: Jul. 16, 2013

(54) MEDICAL DEVICE HAVING AN INTELLIGENT ALERTING SCHEME, AND RELATED OPERATING METHODS

(75) Inventor: Emilian S. Istoc, Winnetka, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 829 days.

(21) Appl. No.: 12/552,821

(22) Filed: Sep. 2, 2009

(65) Prior Publication Data

US 2011/0050428 A1 Mar. 3, 2011

(51) Int. Cl.
*G08B 1/08* (2006.01)

(52) U.S. Cl.
USPC .................... 340/539.15; 340/572.1

(58) Field of Classification Search
USPC 340/573.1, 441, 539.15, 573; 604/65; 600/25
See application file for complete search history.

(56) References Cited

U.S. PATENT DOCUMENTS

| | | |
|---|---|---|
| 3,631,847 A | 1/1972 | Hobbs, II |
| 4,212,738 A | 7/1980 | Henne |
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | DeCant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |

(Continued)

FOREIGN PATENT DOCUMENTS

| | | |
|---|---|---|
| DE | 4329229 | 3/1995 |
| EP | 0319268 | 11/1988 |

(Continued)

OTHER PUBLICATIONS (Animas Corporation, 1999). Animas . . . bringing new life to insulin therapy.

(Continued)

*Primary Examiner* — Shirley Lu
(74) *Attorney, Agent, or Firm* — Ingrassia Fisher & Lorenz, P.C.

(57) ABSTRACT

A portable medical device and related operating methods are provided. One operating method involves a portable medical device that includes a situational awareness sensor. The method begins by detecting an alert condition associated with operation of the portable medical device. In response to the alert condition, the situational awareness sensor performs a scanning operation to obtain sensor data indicative of a current environmental status of the portable medical device. The device can then select a preferred alerting scheme from a plurality of different available alerting schemes, where the preferred alerting scheme is influenced by the sensor data. The device then generates an alert for the alert condition in accordance with the preferred alerting scheme.

17 Claims, 8 Drawing Sheets

U.S. PATENT DOCUMENTS

| | | |
|---|---|---|
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,497,772 A | 3/1996 | Schulman et al. |
| 5,505,709 A | 4/1996 | Funderburk et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,817,990 B2 | 11/2004 | Yap et al. |
| 6,881,551 B2 | 4/2005 | Heller et al. |

| | | | |
|---|---|---|---|
| 6,892,085 B2 | 5/2005 | McIvor et al. | |
| 6,893,545 B2 | 5/2005 | Gotoh et al. | |
| 6,895,263 B2 | 5/2005 | Shin et al. | |
| 6,916,159 B2 | 7/2005 | Rush et al. | |
| 6,932,584 B2 | 8/2005 | Gray et al. | |
| 6,932,894 B2 | 8/2005 | Mao et al. | |
| 6,942,518 B2 | 9/2005 | Liamos et al. | |
| 7,153,263 B2 | 12/2006 | Carter et al. | |
| 7,153,289 B2 | 12/2006 | Vasko | |
| 7,396,330 B2 | 7/2008 | Banet et al. | |
| 2001/0044731 A1 | 11/2001 | Coffman et al. | |
| 2002/0013518 A1 | 1/2002 | West et al. | |
| 2002/0055857 A1 | 5/2002 | Mault et al. | |
| 2002/0082665 A1 | 6/2002 | Haller et al. | |
| 2002/0137997 A1 | 9/2002 | Mastrototaro et al. | |
| 2002/0161288 A1 | 10/2002 | Shin et al. | |
| 2003/0060765 A1 | 3/2003 | Campbell et al. | |
| 2003/0078560 A1 | 4/2003 | Miller et al. | |
| 2003/0088166 A1 | 5/2003 | Say et al. | |
| 2003/0144581 A1 | 7/2003 | Conn et al. | |
| 2003/0152823 A1 | 8/2003 | Heller | |
| 2003/0176183 A1 | 9/2003 | Drucker et al. | |
| 2003/0188427 A1 | 10/2003 | Say et al. | |
| 2003/0199744 A1 | 10/2003 | Buse et al. | |
| 2003/0208113 A1 | 11/2003 | Mault et al. | |
| 2003/0220552 A1 | 11/2003 | Reghabi et al. | |
| 2004/0061232 A1 | 4/2004 | Shah et al. | |
| 2004/0061234 A1 | 4/2004 | Shah et al. | |
| 2004/0064133 A1 | 4/2004 | Miller et al. | |
| 2004/0064156 A1 | 4/2004 | Shah et al. | |
| 2004/0073095 A1 | 4/2004 | Causey, III et al. | |
| 2004/0074785 A1 | 4/2004 | Holker et al. | |
| 2004/0093167 A1 | 5/2004 | Braig et al. | |
| 2004/0097796 A1 | 5/2004 | Berman et al. | |
| 2004/0102683 A1 | 5/2004 | Khanuja et al. | |
| 2004/0111017 A1 | 6/2004 | Say et al. | |
| 2004/0122353 A1 | 6/2004 | Shahmirian et al. | |
| 2004/0167465 A1 | 8/2004 | Mihai et al. | |
| 2004/0263354 A1 | 12/2004 | Mann et al. | |
| 2005/0038331 A1 | 2/2005 | Silaski et al. | |
| 2005/0038680 A1 | 2/2005 | McMahon et al. | |
| 2005/0154271 A1 | 7/2005 | Rasdal et al. | |
| 2005/0192557 A1 | 9/2005 | Brauker et al. | |
| 2005/0267402 A1* | 12/2005 | Stewart et al. | 604/65 |
| 2005/0275626 A1* | 12/2005 | Mueller et al. | 345/156 |
| 2006/0116175 A1* | 6/2006 | Chu | 455/567 |
| 2006/0229694 A1 | 10/2006 | Schulman et al. | |
| 2006/0238333 A1 | 10/2006 | Welch et al. | |
| 2006/0293571 A1 | 12/2006 | Bao et al. | |
| 2007/0088521 A1 | 4/2007 | Shmueli et al. | |
| 2007/0135866 A1 | 6/2007 | Baker et al. | |
| 2007/0253021 A1* | 11/2007 | Mehta et al. | 358/1.15 |
| 2008/0017193 A1* | 1/2008 | Jones et al. | 128/200.23 |
| 2008/0154503 A1 | 6/2008 | Wittenber et al. | |
| 2009/0081951 A1 | 3/2009 | Erdmann et al. | |
| 2009/0082635 A1 | 3/2009 | Baldus et al. | |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | PCT/US02/03299 | 10/2002 |
| WO | WO 03/001329 | 1/2003 |
| WO | WO 03/094090 | 11/2003 |
| WO | WO 2005/065538 A2 | 7/2005 |
| WO | PCT/US2010/045782 | 12/2010 |

OTHER PUBLICATIONS

Bode B W, et al. (1996). Reduction in Severe Hypoglycemia with Long-Term Continuous Subcutaneous Insulin Infusion in Type I Diabetes. Diabetes Care, vol. 19, No. 4, 324-327.

Boland E (1998). Teens Pumping it Up! Insulin Pump Therapy Guide for Adolescents. 2nd Edition.

Brackenridge B P (1992). Carbohydrate Gram Counting A Key to Accurate Mealtime Boluses in Intensive Diabetes Therapy. Practical Diabetology, vol. 11, No. 2, pp. 22-28.

Brackenridge, B P et al. (1995). Counting Carbohydrates How to Zero in on Good Control. MiniMed Technologies Inc.

Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.

Hirsch I B et al. (1990). Intensive Insulin Therapy for Treatment of Type I Diabetes. Diabetes Care, vol. 13, No. 12, pp. 1265-1283.

Kulkarni K et al. (1999). Carbohydrate Counting A Primer for Insulin Pump Users to Zero in on Good Control. MiniMed Inc.

Marcus A O et al. (1996). Insulin Pump Therapy Acceptable Alternative to Injection Therapy. Postgraduate Medicine, vol. 99, No. 3, pp. 125-142.

Reed J et al. (1996). Voice of the Diabetic, vol. 11, No. 3, pp. 1-38.

Skyler J S (1989). Continuous Subcutaneous Insulin Infusion [CSII] With External Devices: Current Status. Update in Drug Delivery Systems, Chapter 13, pp. 163-183. Futura Publishing Company.

Skyler J S et al. (1995). The Insulin Pump Therapy Book Insights from the Experts. MiniMed•Technologies.

Strowig S M (1993). Initiation and Management of Insulin Pump Therapy. The Diabetes Educator, vol. 19, No. 1, pp. 50-60.

Walsh J, et al. (1989). Pumping Insulin: The Art of Using an Insulin Pump. Published by MiniMed•Technologies.

(Intensive Diabetes Management, 1995). Insulin Infusion Pump Therapy. pp. 66-78.

Disetronic My Choice™ D-TRON™ Insulin Pump Reference Manual. (no date).

Disetronic H-TRON® plus Quick Start Manual. (no date).

Disetronic My Choice H-TRONplus Insulin Pump Reference Manual. (no date).

Disetronic H-TRON®plus Reference Manual. (no date).

(MiniMed, 1996). The MiniMed 506. 7 pages. Retrieved on Sep. 16, 2003 from the World Wide Web: http://web.archive.org/web/19961111054527/www.minimed.com/files/506_pic.htm.

(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.

(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.

(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.

(MiniMed Technologies, 1994). MiniMed 506 Insulin Pump User's Guide.

(MiniMed Technologies, 1994). MiniMed™ Dosage Calculator Initial Meal Bolus Guidelines / MiniMed™ Dosage Calculator Initial Basal Rate Guidelines Percentage Method. 4 pages.

(MiniMed, 1996). MiniMed™ 507 Insulin Pump User's Guide.

(MiniMed, 1997). MiniMed™ 507 Insulin Pump User's Guide.

(MiniMed, 1998). MiniMed 507C Insulin Pump User's Guide.

(MiniMed International, 1998). MiniMed 507C Insulin Pump for those who appreciate the difference.

(MiniMed Inc., 1999). MiniMed 508 Flipchart Guide to Insulin Pump Therapy.

(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263, Feb. 1990.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.

Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.
Nishida, Kenro, et al., "Clinical applications of teh wearable artifical endocrine pancreas with the newly designed needle-type glucose sensor," Elsevier Sciences B.V., 1994, pp. 353-358.
Nishida, Kenro, et al., "Development of a ferrocene-mediated needle-type glucose sensor covereed with newly designd biocompatible membrane, 2-methacryloyloxyethylphosphorylcholine -co-n-butyl nethacrylate," Medical Progress Through Technology, vol. 21, 1995, pp. 91-103.
Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.
Reach, G., "A Method for Evaluating in vivo the Functional Characteristics of Glucose Sensors," Biosensors 2, 1986, pp. 211-220.
Shaw, G. W., et al., "In vitro testing of a simply constructed, highly stable glucose sensor suitable for implantation in diabetic patients," Biosensors & Bioelectronics 6, 1991, pp. 401-406.
Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.
Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.
Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.
Shichiri, Motoaki, et al., "Glycaemic Control in a Pacreatectomized Dogs with a Wearable Artificial Endocrine Pancreas," Diabetologia, vol. 24, 1983, pp. 179-184.
Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.
Shichiri, M., et al., "Membrane design for extending the long-life of an implantable glucose sensor," Diab. Nutr. Metab., vol. 2, No. 4, 1989, pp. 309-313.
Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.
Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.
Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, p. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

* cited by examiner

MEDICAL DEVICE HAVING AN INTELLIGENT ALERTING SCHEME, AND RELATED OPERATING METHODS

TECHNICAL FIELD

Embodiments of the subject matter described herein relate generally to electronic devices, such as portable electronic medical devices. More particularly, embodiments of the subject matter relate to alert/alarm methodologies and techniques suitable for use with electronic devices.

BACKGROUND

Portable medical devices having wireless data communication capabilities are becoming increasingly popular, especially for patients that have conditions that must be monitored on a continuous or frequent basis. For example, diabetics are usually required to modify and monitor their daily lifestyle to keep their body in balance, in particular, their blood glucose (BG) levels. Individuals with Type 1 diabetes and some individuals with Type 2 diabetes use insulin to control their BG levels. To do so, diabetics routinely keep strict schedules, including ingesting timely nutritious meals, partaking in exercise, monitoring BG levels daily, and adjusting and administering insulin dosages accordingly. Diabetics may utilize medical devices such as insulin infusion pumps, BG monitors, BG meters, and/or pump controllers to help them manage their diabetes.

Like many electronic devices, portable medical devices are often provided with alarm, alert, and/or reminder features and functions. For example, an insulin infusion pump may sound an alarm when its insulin reservoir needs to be replaced. As another example, BG monitors generate alerts when the patient's BG level goes above or below certain threshold values. Conventional alarm-enabled electronic devices, including some portable medical devices, might generate false alarms from time to time, employ an inappropriate alerting technique (such as a loud siren when the user is sleeping or a vibrating alarm when the device is not being held or carried by the user), or otherwise use only one default alerting scheme. Users typically manage electronic device alarms, alerts, and reminders through configuration menus, preference settings, snooze buttons, etc. Such actions can be inconvenient and time consuming, and sometimes ineffective at reducing annoying or inappropriate alarms.

BRIEF SUMMARY

A method of operating an electronic device is provided. The electronic device includes at least one onboard situational awareness sensor, and the method begins by detecting an alert condition associated with operation of the electronic device. The method continues by using the at least one onboard situational awareness sensor to obtain sensor data indicative of current conditions associated with the electronic device, resulting in collected sensor data. The method then determines, in response to the collected sensor data, a preferred alerting scheme from a plurality of different available alerting schemes. The method continues by generating an alert for the alert condition in accordance with the preferred alerting scheme.

Also provided is a medical device that includes: a first situational awareness sensor configured to obtain first sensor data indicative of a first status for the medical device; a second situational awareness sensor configured to obtain second sensor data indicative of a second status for the medical device; an alert module configured to detect an alert condition associated with operation of the medical device; a decision module configured to process the first sensor data and the second sensor data to determine a preferred alerting scheme for the alert condition; and at least one alert generating element configured to execute the preferred alerting scheme.

Also provided is a method of operating a portable medical device that includes a situational awareness sensor. This method involves: detecting an alert condition associated with operation of the portable medical device; in response to detecting the alert condition, performing a scanning operation with the situational awareness sensor to obtain sensor data indicative of a current environmental status of the portable medical device; selecting a preferred alerting scheme from a plurality of different available alerting schemes, the preferred alerting scheme being influenced by the sensor data; and generating an alert for the alert condition in accordance with the preferred alerting scheme.

Another method of operating a portable medical device is also provided. The portable medical device includes at least one onboard situational awareness sensor, and the method maintains a decision algorithm that selects alerting schemes for the portable medical device, wherein the decision algorithm processes sensor data obtained by the at least one onboard situational awareness sensor to select preferred alerting schemes for alert conditions of the portable medical device. The method generates alerts in accordance with preferred alerting schemes selected by the decision algorithm, obtains information associated with user reactions to the alerts, resulting in obtained user reaction information, and dynamically adapts the decision algorithm in response to the obtained user reaction information.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
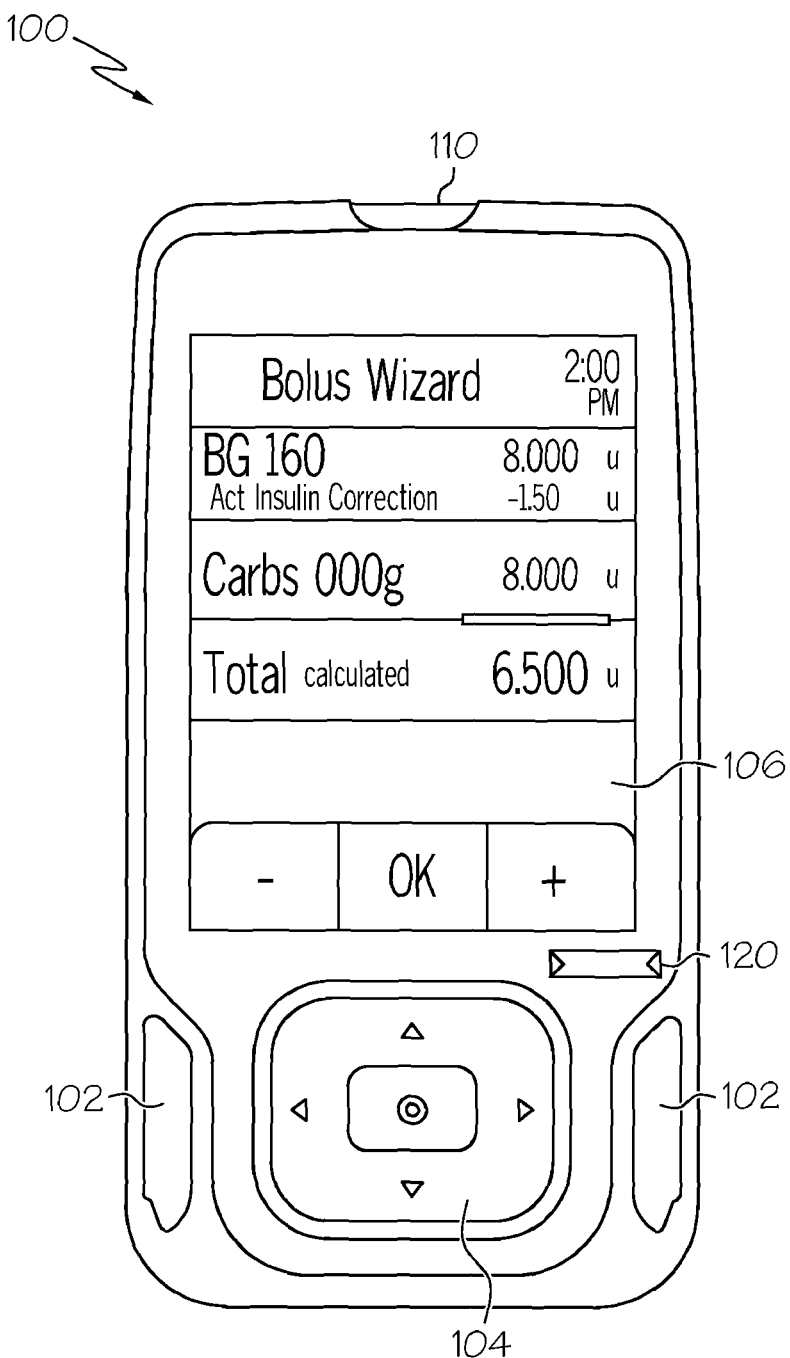
FIG. 1 is a plan view of an exemplary embodiment of a wireless monitor/controller for an infusion pump.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Techniques and technologies may be described herein in terms of functional and/or logical block components and various processing steps. It should be appreciated that such block components may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

For or the sake of brevity, conventional techniques related to infusion system operation, insulin pump and/or infusion set operation, blood glucose sensing and monitoring, signal processing, data transmission, signaling, network control, and other functional aspects of the systems (and the individual operating components of the systems) may not be described in detail here. Examples of infusion pumps and/or communication options may be of the type described in, but not limited to, U.S. Pat. Nos. 4,562,751; 4,685,903; 5,080,653; 5,505,709; 5,097,122; 6,554,798; 6,558,320; 6,558,351; 6,641,533; 6,659,980; 6,752,787; 6,817,990; and 6,932,584, which are herein incorporated by reference. Examples of glucose sensing and/or monitoring devices may be be of the type described in, but not limited to, U.S. Pat. Nos. 6,484,045; 6,809,653; 6,892,085; and 6,895,263, which are herein incorporated by reference.

The systems, methods, and technologies described below can be implemented in an electronic device having one or more alarm, alert, reminder, or notification features that are triggered in response certain conditions, states, status, data values, or the like. For example, an electronic device might be suitably designed to generate an alert when certain operating conditions of the electronic device, or certain environmental conditions, are detected. Although the subject matter described here is applicable to any alarm-enabled or alert-enabled electronic device, the exemplary embodiments are implemented in the form of medical devices, such as portable electronic medical devices. The described medical devices may be associated with a single patient or with multiple patients. The medical devices may be designed to treat one or more different medical conditions, and each medical device might have a specific function in the context of an overall patient treatment or healthcare plan. The non-limiting examples described below relate to a medical device system used to treat diabetes, although embodiments of the disclosed subject matter are not so limited.

A device in an insulin infusion system represents one non-limiting example of an alert-enabled medical device that can utilize the intelligent alerting scheme described herein. An insulin infusion system controls the infusion of insulin into the body of a user, and such a system may include a number of devices that communicate (unidirectional or bidirectional) with each other. For example, one exemplary embodiment of an insulin infusion system might include, without limitation: an insulin infusion pump; at least one physiological characteristic sensor, which may be realized as a continuous glucose sensor transmitter; and one or more wireless controller devices. An insulin infusion system may also include or cooperate with a glucose meter that provides glucose meter data, an infusion set for the insulin infusion pump, and an insulin reservoir (or other means for supplying insulin) for the insulin infusion pump. Moreover, an insulin infusion system may include, cooperate with, or communicate with other devices and subsystems such as, without limitation: a stationary monitor device (e.g., a bedside monitor or a hospital monitor); a vehicle communication system; a wireless-enabled watch that is compatible with the insulin infusion system; etc. Any one (or more) of the devices within an insulin infusion system could leverage the intelligent alerting techniques and methodologies presented here.

Figure 2:
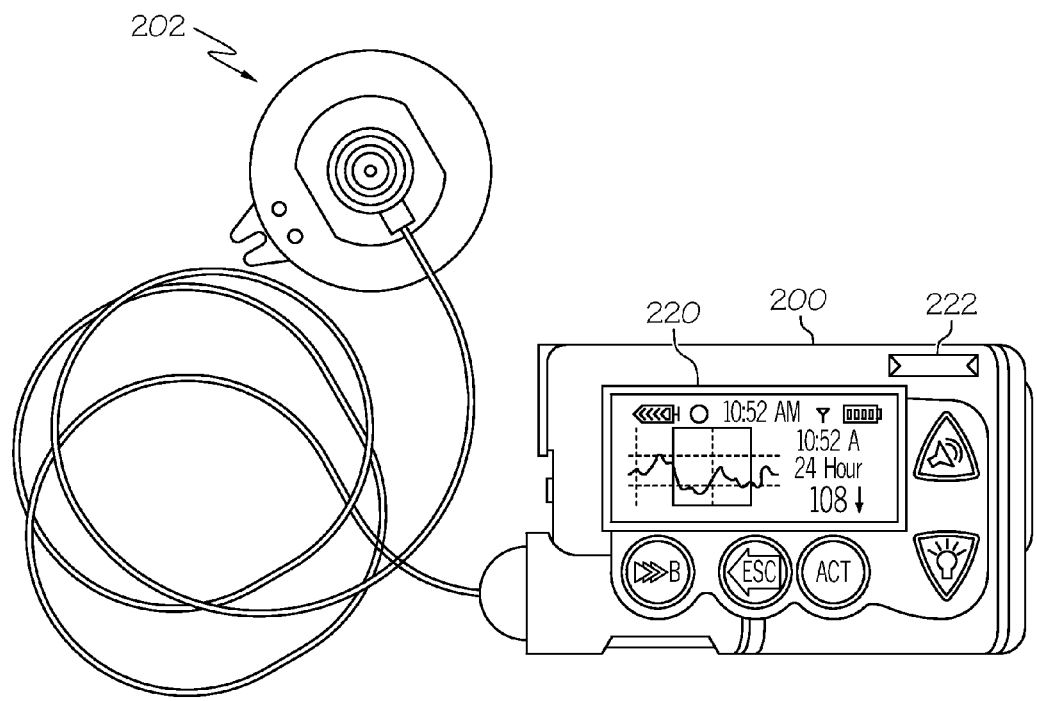
FIG. 2 is a plan view of an exemplary embodiment of an infusion pump and a related infusion set.

FIG. 1 is a plan view of an exemplary embodiment of a wireless monitor/controller 100 for an infusion pump, and FIG. 2 is a plan view of exemplary embodiments of an infusion pump 200 and a related infusion set 202. In practice, the components of an insulin infusion system can be realized using different platforms, designs, and configurations, and the embodiments shown in FIG. 1 and FIG. 2 are not exhaustive or limiting. Moreover, as mentioned previously, other devices in an infusion system, other medical devices designed to address other patient needs, and other portable electronic devices could utilize the smart alarm and alerting schemes presented here. The wireless monitor/controller 100 and the infusion pump 200 are merely two exemplary embodiments.

Referring now to FIG. 1, the wireless monitor/controller 100 is designed as a portable device that can be carried or worn by a user. This particular embodiment includes a human-machine interface (HMI) that includes buttons 102 and a directional pad 104 that can be manipulated by the user. This embodiment also employs a touch screen display element 106 that is responsive to touching and/or physical proximity of an object. The touch screen display element 106 can be used to present various types of information or data to the user, such as, without limitation: the current glucose level of the patient; the time; a graph or chart of the patient's glucose level versus time; device status indicators; alert messages; visual alert indicators; etc.

The buttons 102, directional pad 104, and touch screen display element 106 can be used to administer a bolus of insulin, to change therapy settings, to change user preferences, to select display features, to set or disable alarms and reminders, and the like. Depending upon the configuration settings, options, and/or user preferences, the wireless monitor/controller 100 can be manipulated using the buttons 102 only, the touch screen display element 106 only, or both. In some embodiments, the touch screen display element 106 could be switched on and off if the feature is not desired.

Although not clearly depicted in FIG. 1, the wireless monitor/controller 100 may include a number of features, devices, and/or elements that support the various intelligent alerting schemes described here. In this regard, the wireless monitor/controller 100 can be provided with one or more alert generating elements that provide feedback to the user as needed during operation of the wireless monitor/controller 100. An alert generating element may be suitably configured to generate one or more types of feedback, such as, without limitation: audible feedback; visual feedback; haptic (physical) feedback; temperature feedback; electro-stimulation feedback; magnetic-stimulation feedback; static electricity feedback; or the like. Such feedback can be produced by one or more devices, elements, or features of the wireless monitor/controller 100. For example, the wireless monitor/controller 100 may include any number of the following alert generating elements, without limitation: an audio transducer or speaker 110; a display element (such as the touch screen display element 106); a light-emitting element (such as an LED); a haptic feedback or vibration element, which may be integrated into a display screen or into the touch screen display element 106; etc.

As is well understood, certain alarm or alert conditions detected by the wireless monitor/controller 100 will trigger an alert or alarm. It should be appreciated that a wide variety of triggering conditions may be monitored in an embodiment of the wireless monitor/controller 100. For example, the wireless monitor/controller 100 might be suitably designed to handle any number of the following alert conditions, without limitation: low BG level; high BG level; insulin reservoir low; replace infusion set; low battery; alarm clock; user-entered reminder; or the like. This list of alert/alarm triggers is merely exemplary, and these examples are not intended to limit or otherwise restrict the scope of the subject matter described here.

As described in more detail below, the wireless monitor/controller 100 includes at least one sensor or detector 120 that obtains sensor data used by the intelligent alerting scheme. The sensor data is indicative of current conditions associated with the wireless monitor/controller 100, and/or a status of the wireless monitor/controller 100, and/or any measureable phenomena. For example, the sensor data might be indicative of surrounding environmental conditions, the current date, the current time, the geographic position of the wireless monitor/controller 100, or the like. Accordingly, the sensor 120 (and other sensors that are utilized by the smart alerting scheme) may be referred to herein as a "situational awareness sensor" because the associated sensor data is processed to determine, estimate, or assume the current situational or contextual state of the wireless monitor/controller 100. Notably, a given situational awareness sensor need not be specifically devoted to the intelligent alerting schemes described here. In other words, a given situational awareness sensor could also support other features or functions of the wireless monitor/controller 100, which may not be related to the processing, generation, or handling of alarms, alerts, reminders, or notifications.

Although only one sensor 120 is shown in FIG. 1, certain embodiments will employ a plurality of situational awareness sensors that are suitably configured to detect different measurable phenomena. In practice, a situational awareness sensor could be realized using any desired type of technology that is appropriate for sensing or detecting the specified quantity, condition, state, or phenomena. For example, the onboard situational awareness sensors of the wireless monitor/controller 100 might include one or more of, and in any combination: a sound sensor, a physical proximity sensor, a light intensity sensor, an optical wavelength sensor, a geographic positioning system, a clock, a calendar, a temperature sensor, an accelerometer, a gyroscopic sensor, a motion sensor, a pedometer, an altimeter, a load cell, or the like.

Referring now to FIG. 2, the infusion pump 200 is configured to deliver insulin into the body of the patient via, for example, the infusion set 202. In this regard, the infusion pump 200 may cooperate with an insulin reservoir, which can be a replaceable or refillable fluid reservoir for the insulin. In certain embodiments, the infusion pump 200 and/or the wireless monitor/controller 100 can process received glucose sensor data in an appropriate manner. For example, a device might display the current glucose level derived from the received sensor data and/or generate an alert or otherwise indicate low or high glucose levels. As another example, a device may process the received sensor data for purposes of calibration. As yet another example, the infusion pump 200 may be configured to activate its infusion mechanism in response to the received glucose sensor data.

The illustrated embodiment of the infusion pump 200 is designed to be carried or worn by the patient. This particular embodiment includes a human-machine interface (HMI) that includes several buttons that can be activated by the user. These buttons can be used to administer a bolus of insulin, to change therapy settings, to change user preferences, to select display features, and the like. In some embodiments, the infusion pump 200 includes a suitably configured situational awareness sensor 222 that supports the intelligent alerting techniques described here. Although not required, the illustrated embodiment of the infusion pump 200 includes a display element 220. The display element 220 can be used to present various types of information or data to the user, such as, without limitation: the current glucose level of the patient; the time; a graph or chart of the patient's glucose level versus time; device status indicators; visual alerts, alarms, reminders, or notifications; etc. In some embodiments, the display element 220 is realized as a touch screen display element.

In particular embodiments, the infusion pump 200 includes one or more alert generation elements and one or more situational awareness sensors that support the smart alarm/alert schemes described here. In this regard, the relevant description of the alert/alarm related features and functions of the wireless monitor/controller 100 also applies in an equivalent manner to the infusion pump 200, and such description will not be repeated here for the infusion pump 200.

Depending upon various factors and conditions (e.g., the time, the geographic location of the electronic device, the ambient noise level, whether the electronic device is being carried by the user, whether the electronic device is covered or enclosed by another object), one type of alert or alarm notification may or may not be effective, and may or may not be appropriate. For example, if the user is actually holding the electronic device, then a gentle vibration or a relatively subtle flashing LED pattern might be the most effective and unobtrusive way to alert the user. If, however, the electronic device is in the user's pocket, then visual indicators will be ineffective. As another example, if the electronic device is in a relatively noisy environment, then it may be necessary to generate a relatively loud audible alarm to get the user's attention. In this regard, FIGS. 3-7 are diagrams that illustrate various operating environments for a portable electronic device 300.

Figure 3:
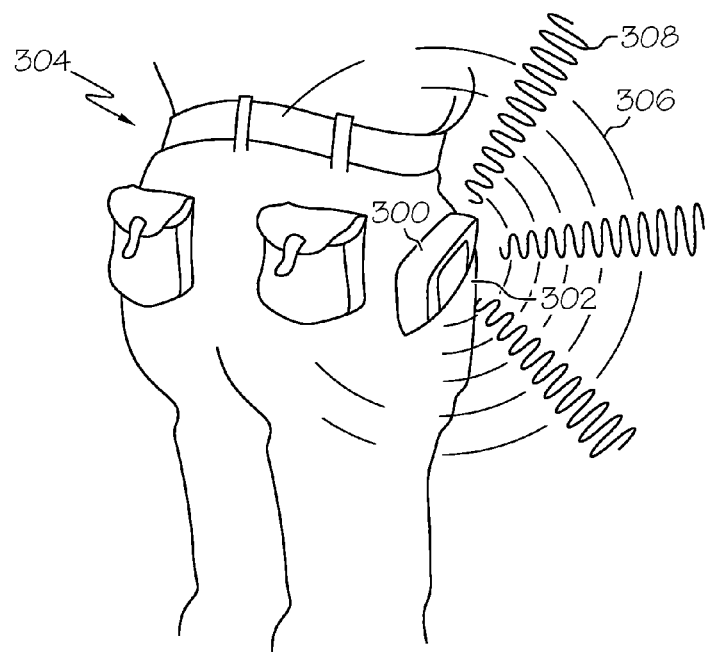
FIGS. 3-7 are diagrams that illustrate various operating environments for a portable electronic device.
Figure 4:
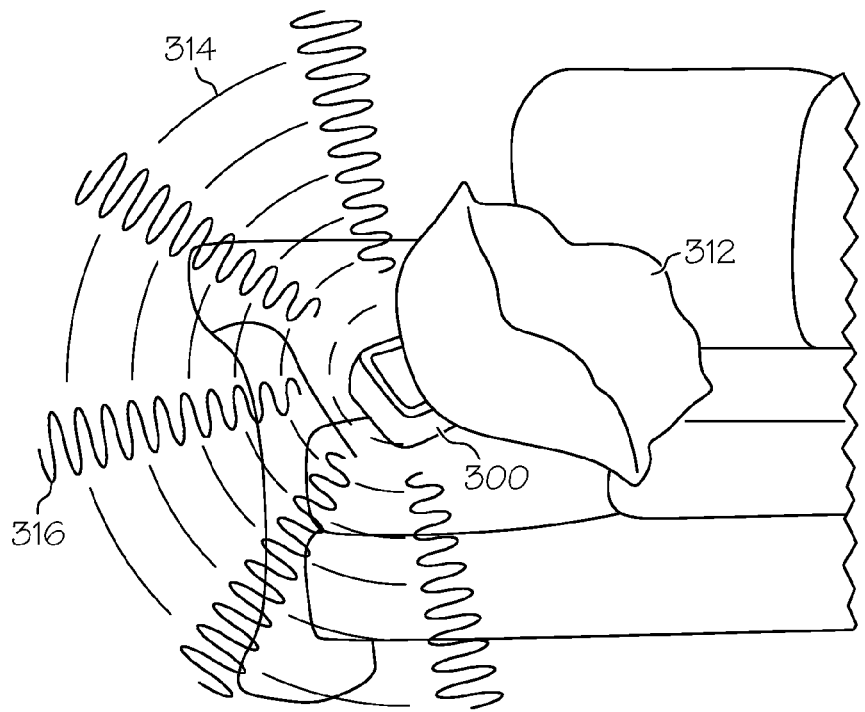
Figure 5:
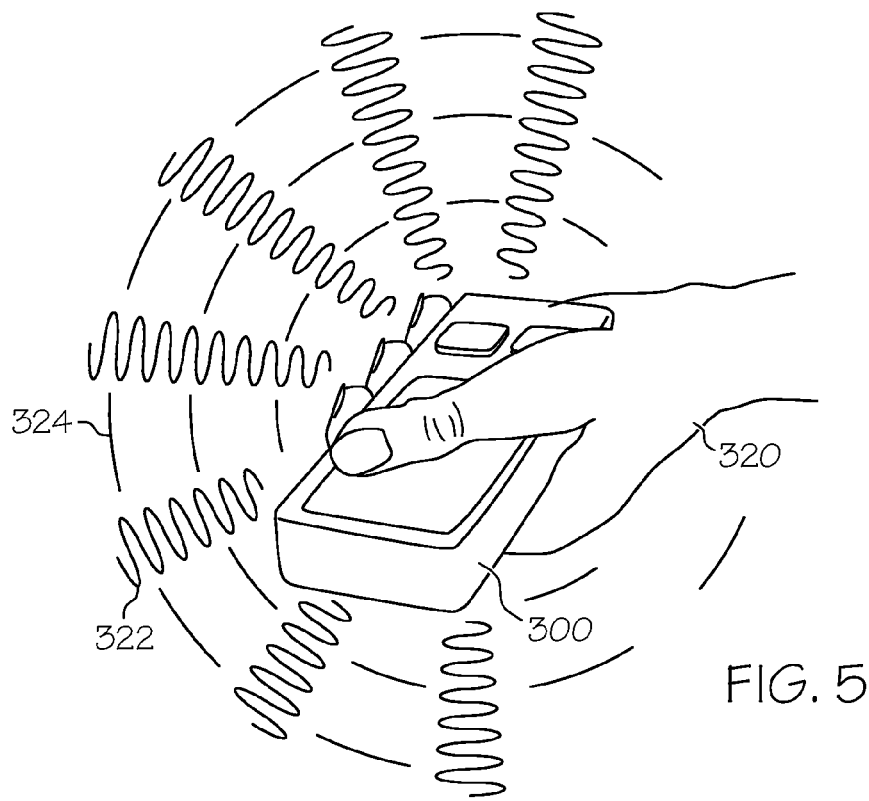
Figure 6:
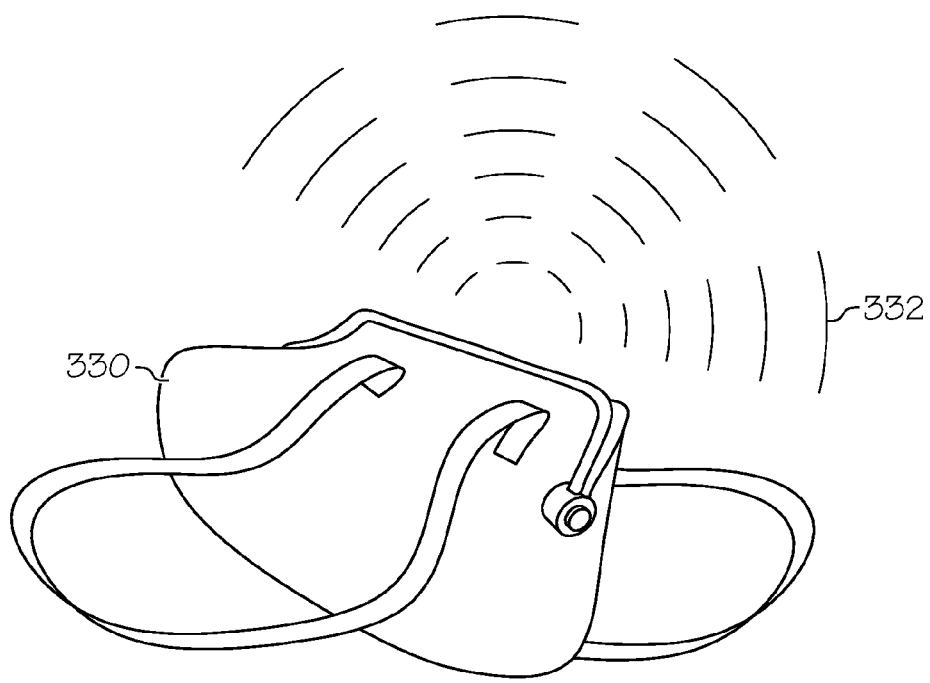
Figure 7:
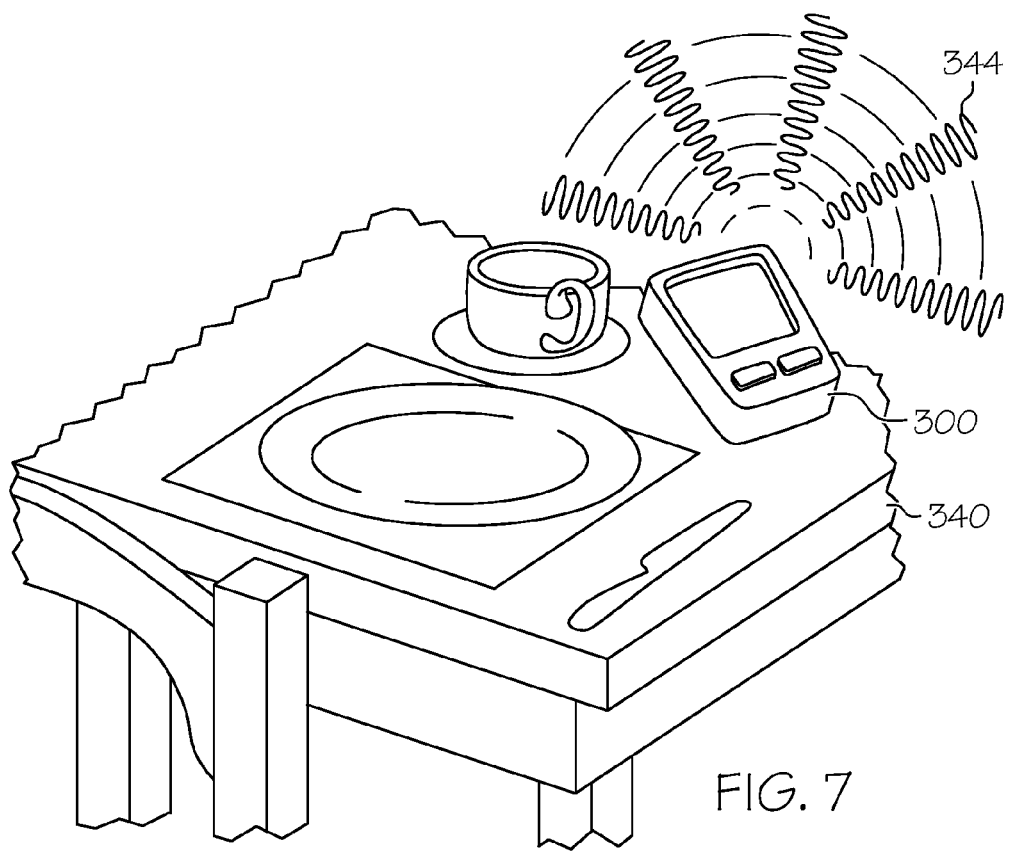

FIG. 3 depicts the electronic device 300 being carried in a pocket 302 of the user 304. Under these conditions, a visual message alert or a visible indicator alert may not be effective. Instead, an audible alert 306 or a vibrating alert 308 may be more appropriate. FIG. 4 depicts the electronic device 300 positioned underneath a pillow 312. In this situation, a haptic feedback alert will be ineffective because the user is not holding or carrying the electronic device 300. Moreover, an audible alert having a nominal or relatively low volume may also be ineffective because the electronic device 300 is covered by the pillow 312, and because the user is not present. Accordingly, it may be better to generate a loud audible alert 314 and/or a bright flashing light display 316 to get the attention of the user (or another person). FIG. 5 shows the electronic device 300 in the hand 320 of a user. Here, a gentle vibration alert 322 or a relatively low volume audible alert 324 may be all that is needed to notify the user. FIG. 6 depicts a scenario where the electronic device (hidden from view) is contained within a purse 330, which is not being carried or held by the user. Under these conditions, it can be assumed that visual and physical feedback will be ineffective. Accordingly, the best alerting scheme for this situation would be to generate a relatively loud audible alert 332 in an attempt to penetrate the enclosure created by the purse 330. FIG. 7 shows the electronic device 300 resting on a table 340 in an open and free manner. In this situation, it may be desirable to generate an audible alert 342 having an average volume and/or a visible alert 344 having nominal characteristics. On the other hand, it may not be wise to generate a vibration alert because doing so might cause the electronic device 300 to shuffle across the table 340 and fall onto the floor.

The environmental conditions described above with reference to FIGS. 3-7 are merely exemplary, and the electronic device 300 could of course be operated under many different conditions, states, statuses, and scenarios. These examples have been presented to illustrate how one alert notification type or scheme may be appropriate and effective under certain situations, yet inappropriate and ineffective under other situations. The intelligent alerting methodologies and techniques described here can be utilized by an electronic device (such as a portable medical device like the controller/programmer illustrated in FIGS. 3-7, or any other medical device) so that a preferred alerting scheme is executed based upon the current state, operating condition, status, and/or environmental conditions as detected by the electronic device itself.

Figure 8:
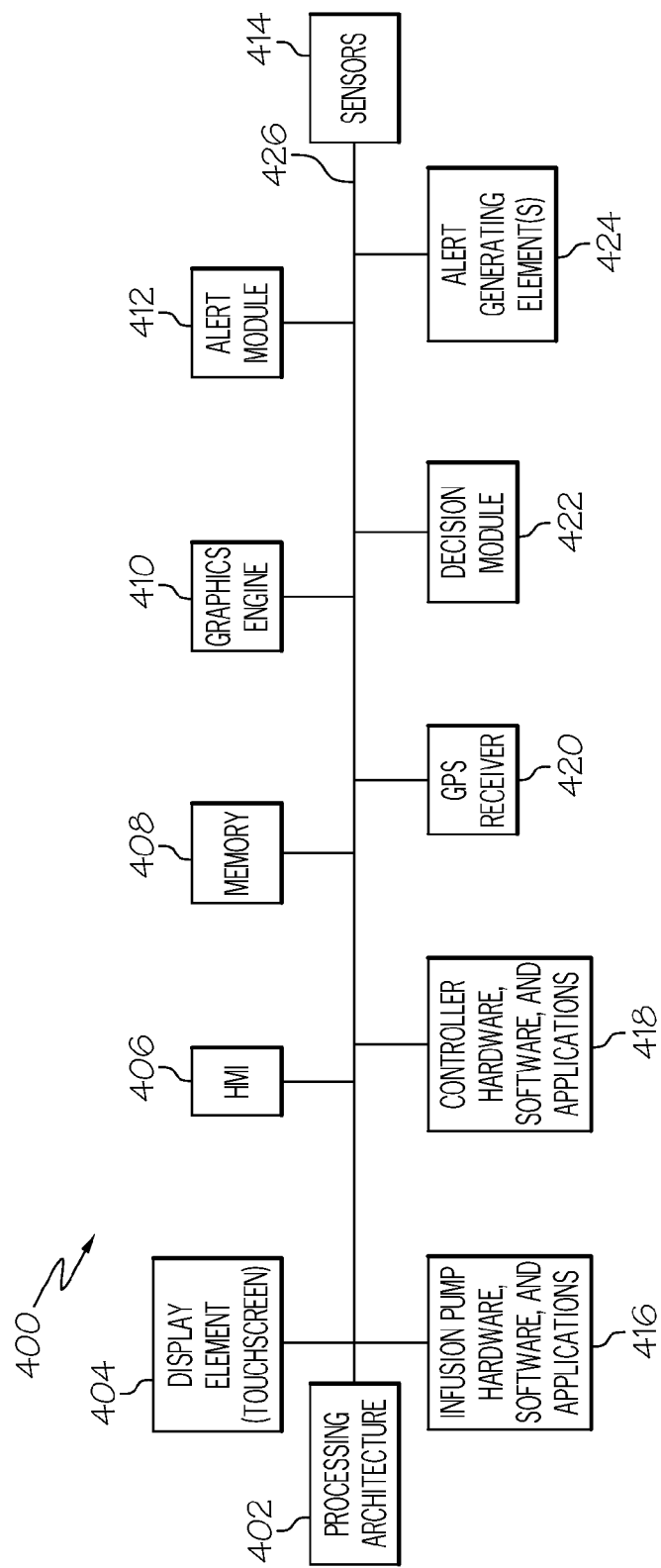
FIG. 8 is a schematic representation of a medical device, which may be realized as an infusion pump, a controller device, or a monitor device.

As mentioned previously, the intelligent alarm techniques described here could be implemented using any electronic device having an alarm, alert, reminder, or notification function. Certain exemplary embodiments, however, are realized in a portable medical device platform. In this regard, FIG. 8 is a schematic representation of a medical device 400, which may be realized as an infusion pump, a therapy delivery device, a monitor, or a controller device suitable for use in a medical device system. The illustrated embodiment of the medical device 400 represents a "full-featured" version; a practical embodiment need not include all of the features, modules, components, and elements depicted in FIG. 8.

This particular embodiment of the medical device 400 generally includes, without limitation: a processing architecture 402, processor, or processor arrangement; a display element 404; at least one human-machine interface (HMI) element 406; a suitable amount of memory 408; a graphics engine 410; an alert module 412; one or more situational awareness sensors 414; infusion pump hardware, software, and applications 416 (included if the medical device 400 represents an infusion pump, and omitted if the medical device 400 does not include infusion pump functionality); controller hardware, software, and applications 418 (included if the medical device 400 represents a controller device, and omitted if the medical device 400 represents an infusion pump that lacks native controller functionality); a global positioning system (GPS) receiver 420; a decision module 422; and one or more alert generating elements 424. The elements of the medical device 400 may be coupled together via a bus 426 or any suitable interconnection architecture or arrangement that facilitates transfer of data, commands, power, etc.

Those of skill in the art will understand that the various illustrative blocks, modules, circuits, and processing logic described in connection with the medical device 400 (and other devices, elements, and components disclosed here) may be implemented in hardware, computer software, firmware, a state machine, or any combination of these. To clearly illustrate this interchangeability and compatibility of hardware, firmware, and software, various illustrative components, blocks, modules, circuits, and processing steps may be described generally in terms of their functionality. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting.

The processing architecture 402 may be implemented or performed with a general purpose processor, a content addressable memory, a digital signal processor, an application specific integrated circuit, a field programmable gate array, any suitable programmable logic device, discrete gate or transistor logic, discrete hardware components, or any combination designed to perform the functions described here. A processor device may be realized as a microprocessor, a controller, a microcontroller, or a state machine. Moreover, a processor device may be implemented as a combination of computing devices, e.g., a combination of a digital signal processor and a microprocessor, a plurality of microprocessors, one or more microprocessors in conjunction with a digital signal processor core, or any other such configuration.

The processing architecture 402 may include one processor device or a plurality of cooperating processor devices. Moreover, a functional or logical module/component of the medical device 400 might actually be realized or implemented with the processing architecture 402. For example, the graphics engine 410, the alert module 412, and/or the decision module 422 may be implemented in, or be executed by, the processing architecture 402.

The display element 404 represents a primary graphical interface of the medical device 400. The display element 404 may leverage known CRT, plasma, LCD, TFT, and/or other display technologies. The actual size, resolution, and operating specifications of the display element 404 can be selected to suit the needs of the particular application. Notably, the display element 404 may include or be realized as a touch screen display element that can accommodate touch screen techniques and technologies. In practice, the display element 404 may be influenced by the graphics engine 410, and driven by a suitable display driver, to enable the medical device 400 to display physiological patient data, status information for infusion pumps, status information for continuous glucose sensor transmitters, clock information, alarms, alerts, and/or other information and data received or processed by the medical device 400. In this regard, the display element 404 could be configured to receive image rendering display commands from the graphics engine 410 and, in response thereto, render visual representations of physiological characteristic data (e.g., glucose levels), render menu screens, render text-based alerts, display other visual indicia of an alert, alarm, or reminder condition, and render other graphical representations and visual displays as needed during the operation of the medical device 400.

HMI elements 406 represent the user interface features of the medical device 400. Thus, HMI elements 406 may include a variety of items such as, without limitation: a keypad, keys, buttons, a keyboard, switches, knobs (which may be rotary or push/rotary), a touchpad, a microphone suitably adapted to receive voice commands, a joystick, a pointing device, an alphanumeric character entry device or touch element, a trackball, a motion sensor, a lever, a slider bar, a virtual writing tablet, or any device, component, or function that enables the user to select options, input information, or otherwise control the operation of the medical device 400. As will become apparent from the following description, a particular HMI element 406 could also serve as a situational awareness sensor 414 in some embodiments (and vice versa). The medical device 400 can detect manipulation of, or interaction with, the HMI elements 406 and react in an appropriate manner. For example, a user could interact with the HMI elements 406 to control the delivery of therapy (e.g., insulin infusion) to a patient via a therapy delivery device under the control of the medical device 400.

The memory 408 may be realized as RAM memory, flash memory, EPROM memory, EEPROM memory, registers, a hard disk, a removable disk, a CD-ROM, or any other form of storage medium known in the art. In this regard, the memory 408 can be coupled to the processing architecture 402 such that the processing architecture 402 can read information from, and write information to, the memory 408. In the alternative, the memory 408 may be integral to the processing architecture 402. As an example, the processing architecture 402 and the memory 408 may reside in an ASIC. A functional or logical module/component of the medical device 400 might be realized using program code that is maintained in the memory 408. For example, the graphics engine 410, the alert module 412, and/or the decision module 422 may have associated software program components that are stored in the memory 408. Moreover, the memory 408 can be used to store data utilized to support the operation of the medical device 400, as will become apparent from the following description. For example, the memory 408 could be used to maintain a lookup table, a decision tree, and/or rules that govern the processing of data obtained by the sensors 414.

A number of visual-based and illumination-based alert/alarm features and characteristics are described in more detail below. Accordingly, the graphics engine 410 may be suitably configured to perform image, graphics, and/or video processing as needed to support the intelligent alerting operation of the medical device 400. The graphics engine 410 cooperates with the display driver (not shown) of the medical device 400 to control and manage the rendering of graphical information on the display element 404. For example, the graphics engine 410 generates image rendering display commands associated with items to be displayed (such as text-based alert data, screen areas used for light or illumination elements, or the like), and the display element 404 receives the image rendering display commands and, in response thereto, renders corresponding graphics as needed.

The alert module 412 is suitably configured to detect alert conditions, alarm conditions, notification conditions, reminder conditions, and/or other conditions that trigger or otherwise prompt the medical device 400 to generate corresponding alerts, alarms, notifications, reminders, flags, or the like. In certain embodiments, the conditions detected by the alert module 412 are associated with the operation, status, state, functionality, or characteristics of the medical device 400. Thus, the alert module 412 could be suitably configured to detect one or more of the following conditions, without limitation: low BG level; high BG level; insulin reservoir low; replace infusion set; low battery; alarm clock; user-entered reminder; or the like. Alternatively (or additionally), the conditions detected by the alert module 412 could be associated with the operation, status, state, functionality, or characteristics of another device, system, or subsystem that communicates with the medical device 400. Alternatively (or additionally), the conditions detected by the alert module 412 could be associated with a user or an operator of the medical device 400 (or a user or operator of a device that communicates with the medical device 400). Alternatively (or additionally), the conditions detected by the alert module 412 could be associated with user-entered information, e.g., personal reminders, notes, etc.

Each situational awareness sensor 414 samples, detects, senses, or otherwise obtains respective sensor data, which can be used for the intelligent alerting methodologies described here. As mentioned above, the collected sensor data might be indicative of various measurable phenomena, characteristics, environmental conditions, or the like. For example, a situational awareness sensor 414 could be realized as a sound sensor (such as a microphone or other transducer) that obtains ambient sound data that is indicative of sound level near the medical device 400. As another example, a situational awareness sensor 414 could be implemented as a physical proximity sensor (such as an infrared, sonic, or magnetic emitter/detector, or a capacitive or resistive sensor) that obtains proximity data that is indicative of the proximity of objects near the medical device 400. In certain embodiments, the medical device 400 could employ a plurality of physical proximity sensors that enable it to detect the presence of objects from different sides of the medical device 400 (e.g., the front, back, the top edge, the bottom edge, or the side edges).

In certain embodiments, the medical device 400 utilizes optical or light sensors. For instance, a situational awareness sensor 414 could be realized as an optical wavelength sensor that obtains wavelength (or frequency) data for ambient light near the medical device 400. The same (or a separate) situational awareness sensor 414 could also be utilized as a light intensity sensor that obtains intensity data that is indicative of ambient light intensity near the medical device 400.

As mentioned above, an embodiment of the medical device 400 might leverage one or more sources of date, time, and position data. For example, a situational awareness sensor 414 could be realized as a GPS sensor or receiver that obtains position data that is indicative of the present geographic position of the medical device 400. Alternatively, the medical device 400 could receive GPS data from an external source. The same (or a separate) situational awareness sensor 414 could also be realized as a clock that obtains time data for the medical device 400. The same (or a separate) situational awareness sensor 414 could also be realized as a calendar that obtains calendar data for the medical device 400.

In some embodiments, the medical device 400 could include one or more situational awareness sensors 414 that detect conditions, forces, or physical phenomena applied to or imparted on the medical device 400. For example, a situational awareness sensor 414 could be realized as a load cell that obtains load data indicative of loading on the medical device 400. In this regard, loading on the medical device 400 may result if it is placed in a pocket, if the user is sitting or sleeping on the medical device 400, if the medical device 400 is covered by a blanket or other object, or the like. Situational awareness sensors 414 could also be utilized to detect, sense, or sample, without limitation: the ambient temperature surrounding the medical device 400; the operating temperature of the medical device 400; the acceleration, velocity, or motion of the medical device 400; the orientation of the medical device 400 relative to some reference direction (e.g., whether the medical device 400 is being held upside-down, sideways, face-down, or the like); the number of steps taken by the user of the medical device 400 during a reference period of time; the altitude of the medical device 400; the attitude of the medical device 400; etc. The various examples of situational awareness sensors 414 provided here are not intended to be exhaustive or to otherwise limit or restrict the scope or application of the described subject matter.

The infusion pump hardware, software, and applications 416 are utilized to carry out features, operations, and functionality that might be specific to an insulin pump implementation. Again, the infusion pump hardware, software, and applications 416 need not be deployed if the medical device 400 is realized as a controller device having no infusion pump. Notably, the infusion pump hardware, software, and applications 416 may include or cooperate with an infusion set and/or a fluid reservoir (not shown). The infusion pump hardware, software, and applications 416 may leverage known techniques to carry out conventional infusion pump functions and operations, and such known aspects will not be described in detail here.

The controller hardware, software, and applications 418 are utilized to carry out features, operations, and functionality that might be specific to a medical device controller implementation. Again, the controller hardware, software, and applications 418 need not be deployed if the medical device 400 is realized as a medical device having no native control capabilities. The controller hardware, software, and applications 418 may leverage known techniques to carry out conventional controller and/or monitor device functions and operations, and such known aspects will not be described in detail here.

The GPS receiver 420 may be any commercial civilian grade receiver. In accordance with known methodologies and techniques, the GPS receiver 420 obtains geographic position data (also referred to as GPS data) corresponding to the geographic position of the medical device 400. The GPS data may indicate a location of the medical device 400 in terms of longitude and latitude measurements. The GPS receiver 420 may also provide the medical device 400 with the current date, the current time, the current time zone, and other pertinent information. In this regard, the GPS receiver 420 may also serve as a situational awareness sensor 414 that provides time data, calendar data, GPS data, and other information that can be used by the smart alerting schemes described here. The geographic position data obtained from the GPS receiver 420 can be used to provide a variety of location-dependent information to the user of the medical device 400, and the relevance of such geographic position data is discussed in more detail below.

The decision module 422 is suitably configured to process sensor data collected by the situational awareness sensors 414 (and possibly other sources of data that may be incorporated into the medical device 400 or made available to the medical device 400). The decision module 422 processes or analyzes the sensor data to determine, select, identify, or choose a preferred alerting scheme for an alert condition of the medical device 400. The preferred alerting scheme is selected from a plurality of different available alerting schemes. In certain embodiments, the decision module 422 includes or cooperates with a decision tree for the sensor data. The decision tree is traversed (using the collected sensor data) to determine the preferred alerting scheme, as described in more detail below with reference to FIG. 9. In particular embodiments, the decision module 422 dynamically adapts the decision tree in response to user reaction to the preferred alerting scheme (as described in more detail below with reference to FIG. 11). Alternatively, the decision module 422 could maintain and utilize an appropriate decision algorithm or function that selects the preferred alerting scheme in a manner that is influenced by the collected sensor data.

The alert generating elements 424 can execute an alerting scheme for an alert condition, under the control of the alert module 412. In practice, the preferred alerting scheme for a given alert, alarm, reminder, or notification may involve one alert generating element 424 (e.g., a speaker) or a plurality of different alert generating elements 424 (e.g., a speaker and a display). Depending upon the implementation, the medical device 400 might employ one or more of the following types of alert generating elements 424, individually or in any combination, and without limitation: an audio transducer or speaker; a display element (such as a touch screen display element); a light-emitting element (such as an LED); a haptic feedback or vibration element, which may be integrated into a display screen or into the touch screen display element; etc.

If the medical device 400 utilizes an audio alert generating element 424, then an alert could be generated by annunciating an audible alert having audible characteristics that are determined by the preferred alerting scheme. If the medical device 400 utilizes its display element 404 as an alert generating element 424, then an alert could be generated by displaying an alert message having content that is determined by the preferred alerting scheme. For example, the display element 404 could be used to display text messages, symbols, or other graphical indicia of the alert condition. If the medical device 400 utilizes a visual indicator as an alert generating element 424, then an alert could be generated (at least in part) as a visible alert having visual characteristics that are determined by the preferred alerting scheme. If the medical device 400 utilizes a haptic feedback device as an alert generating element 424, then an alert could be generated (at least in part) as a physical feedback alert having haptic characteristics that are determined by the preferred alerting scheme.

In practice, the medical device 400 intelligently determines a preferred alerting scheme for each detected alert condition. As used here, an "alerting scheme" may involve one or more different alert generating elements 424 in any desired combination. Thus, an alerting scheme may activate a single alert generating element 424, or it may activate a plurality of different alert generating elements 424 in a defined sequence. Another alerting scheme could activate a plurality of different alert generating elements 424 concurrently or simultaneously during a specified period of time. Moreover, the medical device 400 could modulate, vary, or adjust the output of any given alert generating element 424 as desired or needed. In this regard, an alert generating element 424 could be controlled to escalate at least one characteristic of its alert notification in a manner defined by the preferred alerting scheme. For example, the volume, tone, or frequency of an audible alert notification could be escalated or otherwise altered in a manner designed to capture the user's attention. As another example, the output magnitude of a shaker or vibration element could be increased or escalated over a designated period of time or until the alert is disabled by a user.

An alerting scheme may call for any number of different alert notification types, in any order, pattern, or sequence. As used here, an "alert notification type" may correspond to the type of alert generating element 424 and/or to the characteristics or qualities of the output generated by a single alert generating element 424. In certain embodiments of the medical device 400, a single alert can be generated by switching from a first alert notification type to a second notification type in a manner defined by the preferred alerting scheme. For instance, the alert generating elements 424 could be activated in response to a detected alert condition such that they generate a first alert notification type (e.g., audible, visual, haptic) followed by a second and different alert notification type. As another example, a single LED-based alert generating element 424 could be controlled such that it generates a first alert notification type (e.g., light having a first predefined intensity, flashing pattern, and/or flashing frequency) followed by a second alert notification type (e.g., light having a second predefined intensity, flashing pattern, and/or flashing frequency). Accordingly, the preferred alerting scheme might call for a particular sequence of different alert notification types, and that sequence can be generated over a designated period of time or until the alert/alarm is disabled by a user.

If the medical device 400 includes a sound sensor that measures ambient sound levels, then the preferred alerting scheme might call for a first alert notification type when the ambient sound data indicates higher sound levels near the medical device 400, and a second alert notification type when the ambient sound data indicates lower sound levels near the medical device 400. Thus, the medical device 400 could automatically increase the volume of audible alerts as needed to compensate for noisy environments. As another example, the medical device 400 might determine that audible alerts will be ineffective in very noisy environments and, accordingly, instead call for vibration and/or light-emitting alerts.

If the medical device 400 includes a physical proximity sensor that detects the presence of objects near or surrounding the medical device 400, then the preferred alerting scheme might call for a first alert notification type when the proximity data indicates longer distances relative to the medical device 400, and a second alert notification type when the proximity data indicates shorter distances relative to the medical device 400. Thus, if the medical device 400 detects an object in close proximity to itself, then it might assume that it is enclosed, covered, or surrounded by something (e.g., a purse, a pocket, or a blanket). Under such conditions, the medical device 400 can generate a relatively loud audible alert. In contrast, if the medical device 400 determines that it is resting on a table or other surface, then it might assume that the user is neither holding, carrying, nor resting on the medical device 400. Accordingly, the medical device 400 may decide to generate a conspicuous visual alert under such conditions.

If the medical device 400 includes an optical wavelength sensor that measures the wavelength or frequency of ambient light, then the preferred alerting scheme might call for a first alert notification type when the wavelength/frequency data indicates artificial ambient light near the medical device 400, and a second alert notification type when the wavelength/frequency data indicates natural ambient light near the medical device 400. Thus, the medical device 400 could automatically increase the volume of audible alerts and/or the brightness of displayed alerts if natural light is detected (indicating that the medical device 400 is outdoors). In contrast, if artificial light is detected (indicating that the medical device 400 is indoors), then the preferred alerting scheme may instead call for lower audible volume and/or lower brightness.

If the medical device 400 uses the GPS receiver 420 as a situational awareness sensor 414 to obtain position data indicative of the present geographic position of the medical device 400, then the preferred alerting scheme might call for different alert notification types, based upon the position data. In this regard, the medical device 400 could maintain a map database or table that includes different geographic locations, descriptive information related to the locations (e.g., whether the location is a place of business, the user's office, a conference room, a restaurant, etc.), and preferred alerting schemes corresponding to the locations. For example, if the GPS data indicates that the medical device 400 is located in a movie theater, then the preferred alerting scheme might disable all audible and light-emitting alerts and instead rely on haptic feedback alerts. As another example, if the GPS data indicates that the medical device 400 is located in the user's office or work cubicle, then the preferred alerting scheme might generate audible alerts. As yet another example, if the GPS data indicates that the medical device 400 is located in a nightclub, then the preferred alerting scheme might generate relatively loud audible alerts in combination with haptic feedback and conspicuous light-emitting alerts.

If the medical device 400 uses a clock and/or a calendar as a situational awareness sensor 414 to obtain time and/or calendar data for the medical device 400, then the preferred alerting scheme might call for different alert notification types, based upon the current time and/or date. For example, the medical device 400 might employ one alerting scheme during waking hours, and a different alerting scheme during the user's normal sleeping hours. As another example, the medical device 400 might specify one alerting scheme during weekdays, and a different alerting scheme during weekends.

If the medical device 400 uses a load cell as a situational awareness sensor 414 to obtain load data indicative of loading on the medical device 400, then the preferred alerting scheme might call for a first alert notification type when the load data indicates higher loading on the medical device 400, and a second alert notification type when the load data indicates lower loading on the medical device 400. For example, if the load data suggests that the medical device 400 is in the open without any objects covering it, then the preferred alerting scheme might call for loud audible alerts, no vibration, and relatively conspicuous visual alerts. If, however, the load data indicates that the user might be resting or sleeping on the medical device 400, then the preferred alerting scheme might call for vibrating alerts and relatively loud audible alerts. As another example, if the load data indicates that the user is holding the medical device 400, then the preferred alerting scheme might call for a gentle vibration alert or a low volume audible alert.

Figure 9:
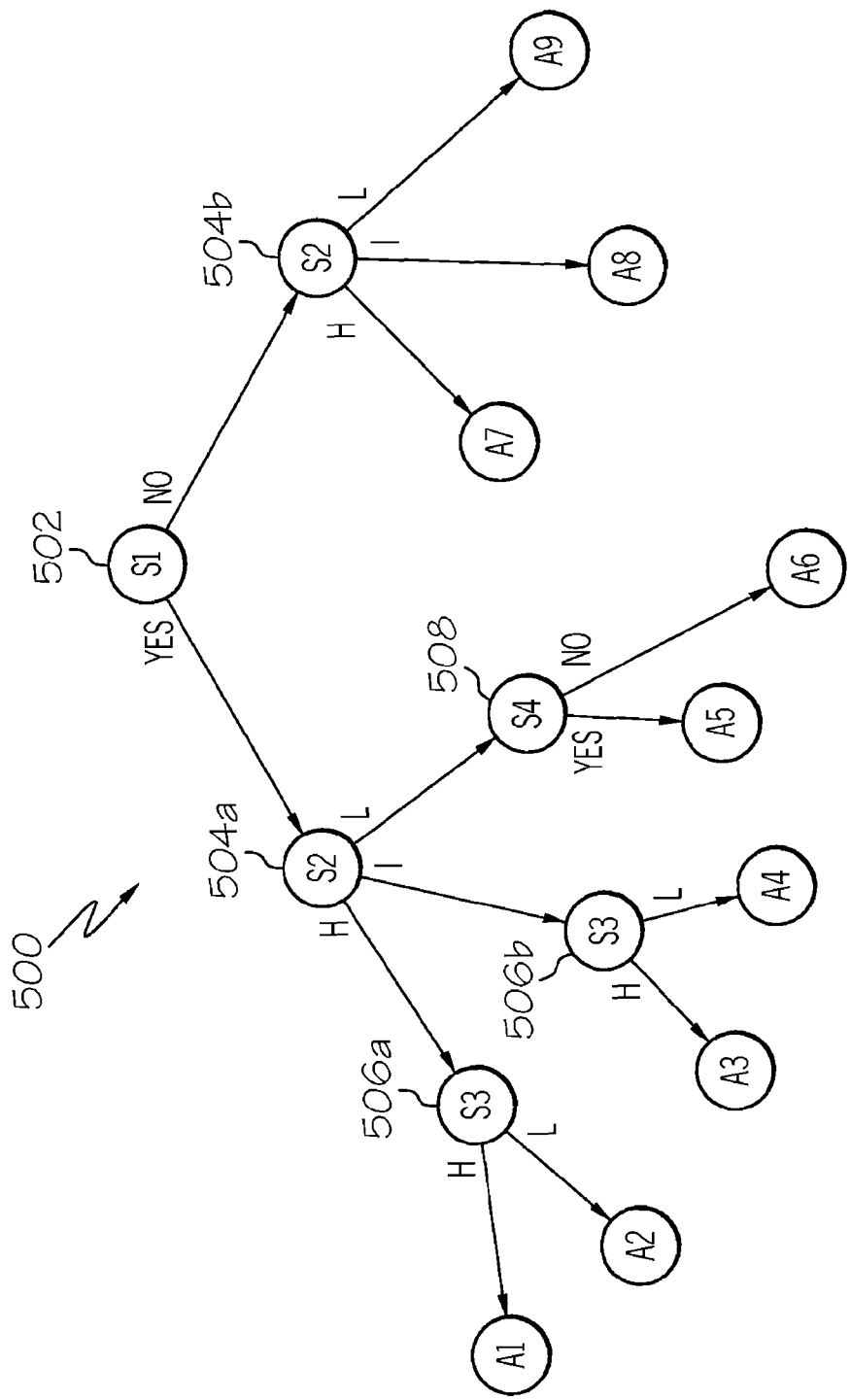
FIG. 9 is a diagram that represents an exemplary decision tree that could be used to select a preferred alerting scheme for a medical device.

FIG. 9 is a diagram that represents an exemplary decision tree 500 that could be used to select a preferred alerting scheme for a medical device such as the medical device 400. This particular decision tree 500 is merely one of many different decision trees that could be implemented by an embodiment of a medical device. An actual decision tree utilized by a medical device might be more or less complex and, as described below, might be dynamically adaptable such that the host medical device can be trained and optimized in an ongoing manner in response to user reactions to the selected alerting schemes.

This embodiment of the decision tree 500 assumes that the medical device uses four different situational awareness sensors (labeled S1, S2, S3, and S4), although any suitable number of sensors may be utilized. For this example, the data obtained from the first sensor 502 results in two possible outcomes (labeled Yes and No), the data obtained from the second sensor 504 results in three possible outcomes (labeled High, Intermediate, and Low), the data obtained from the third sensor 506 results in two possible outcomes (labeled High and Low), and the data obtained from the fourth sensor 508 results in two possible outcomes (labeled Yes and No). FIG. 9 depicts a relatively simple example where some sensors are associated with two output branches and others are associated with three output branches. Depending upon the embodiment, however, any number of potential decision branches corresponding to different possible outcomes may be associated with a given situational awareness sensor.

For this embodiment, the decision tree 500 is traversed using the sensor data to arrive at one of nine possible alerting schemes (labeled A1-A9). In practice, any number of different alerting schemes could be used. Moreover, unique alerting schemes need not be associated with each possible decision path (as depicted in FIG. 9). In other words, two different decision paths could point to the same alerting scheme if so desired. For this particular example, the A1 alerting scheme is selected if: (1) the sensor data from the first sensor 502 satisfies the "Yes" criteria; (2) the sensor data from the second sensor 504a satisfies the "High" criteria; and (3) the sensor data from the third sensor 506a satisfies the "High" criteria. In contrast, the A2 alerting scheme is selected if: (1) the sensor data from the first sensor 502 satisfies the "Yes" criteria; (2) the sensor data from the second sensor 504a satisfies the "High" criteria; and (3) the sensor data from the third sensor 506a satisfies the "Low" criteria. The A3 alerting scheme is selected if: (1) the sensor data from the first sensor 502 satisfies the "Yes" criteria; (2) the sensor data from the second sensor 504a satisfies the "Intermediate" criteria; and (3) the sensor data from the third sensor 506b satisfies the "High" criteria. The A4 alerting scheme is selected if: (1) the sensor data from the first sensor 502 satisfies the "Yes" criteria; (2) the sensor data from the second sensor 504a satisfies the "Intermediate" criteria; and (3) the sensor data from the third sensor 506b satisfies the "Low" criteria.

For this example, the A5 alerting scheme is selected if: (1) the sensor data from the first sensor 502 satisfies the "Yes" criteria; (2) the sensor data from the second sensor 504a satisfies the "Low" criteria; and (3) the sensor data from the fourth sensor 508 satisfies the "Yes" criteria. However, the A6 alerting scheme is selected if: (1) the sensor data from the first sensor 502 satisfies the "Yes" criteria; (2) the sensor data from the second sensor 504a satisfies the "Low" criteria; and (3) the sensor data from the fourth sensor 508 satisfies the "No" criteria.

For this embodiment of the decision tree, the A7 alerting scheme is selected if: (1) the sensor data from the first sensor 502 satisfies the "No" criteria; and (2) the sensor data from the second sensor 504b satisfies the "High" criteria. The A8 alerting scheme is selected if: (1) the sensor data from the first sensor 502 satisfies the "No" criteria; and (2) the sensor data from the second sensor 504b satisfies the "Intermediate" criteria. Finally, the A9 alerting scheme is selected if: (1) the sensor data from the first sensor 502 satisfies the "No" criteria; and (2) the sensor data from the second sensor 504b satisfies the "Low" criteria. In contrast to the alerting schemes that result from the "Yes" branch of the first sensor 502 (A1-A6, which are all influenced by the output of three sensors), the alerting schemes that result from the "No" branch of the first sensor 502 (A7-A9) are influenced by the output of only two sensors. Again, the number of situational awareness sensors that influence a particular alerting scheme can vary depending upon the particular embodiment, application, user preferences, and other practical operating factors.

Operation Example

Figure 10:
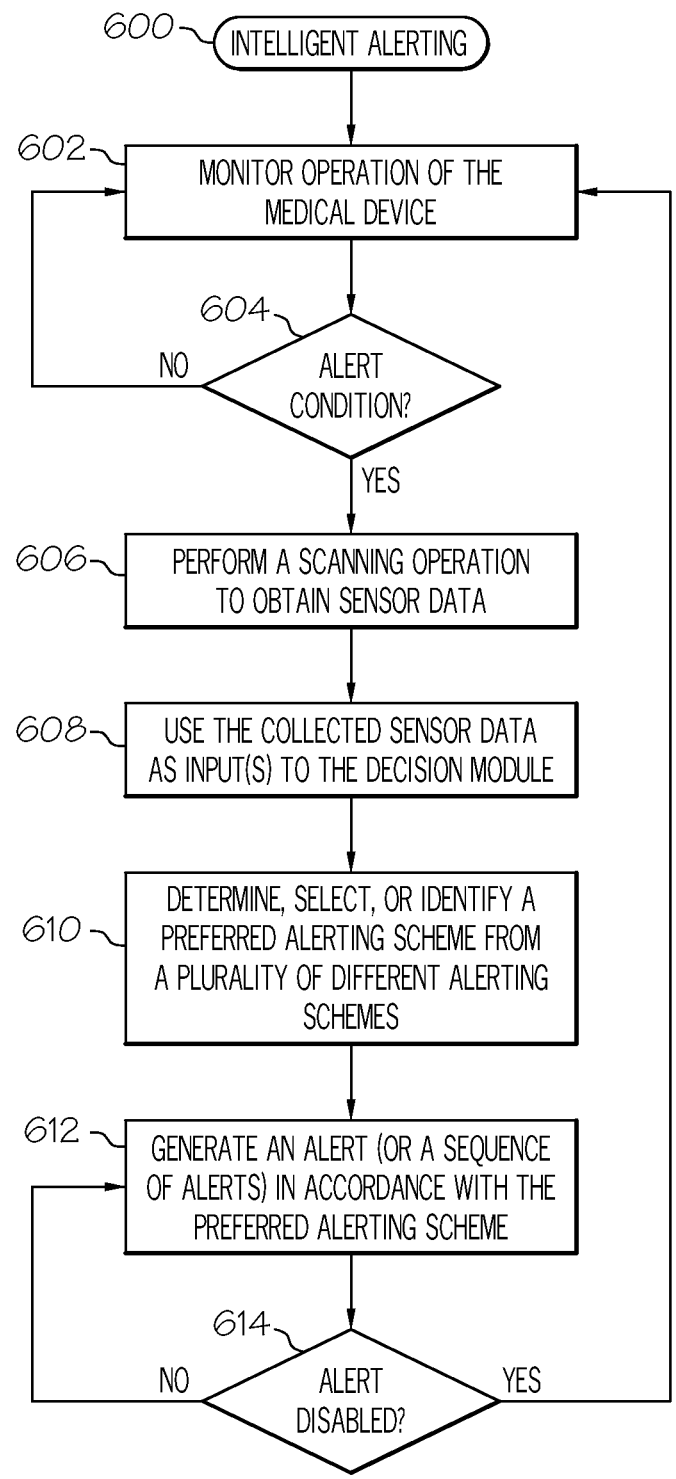
FIG. 10 is a flow chart that illustrates an embodiment of an intelligent alerting process suitable for use with a portable medical device.
Figure 11:
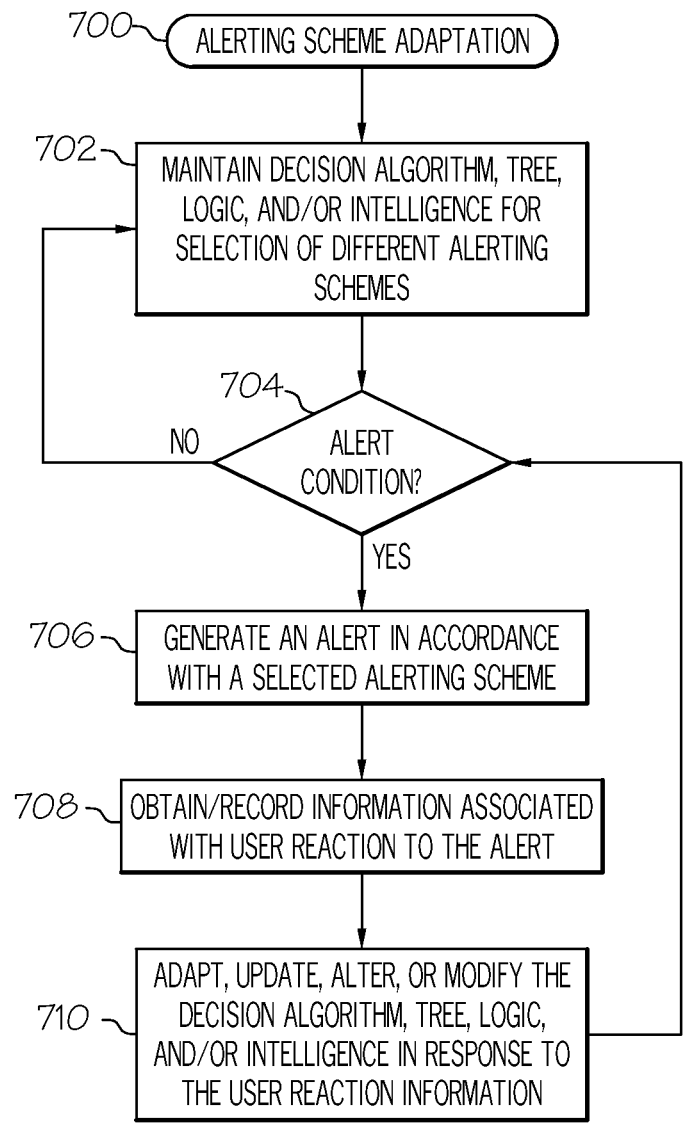
FIG. 11 is a flow chart that illustrates an embodiment of an alerting scheme adaptation process suitable for use with a portable medical device.

FIG. 10 is a flow chart that illustrates an embodiment of an intelligent alerting process 600, and FIG. 11 is a flow chart that illustrates an embodiment of an alerting scheme adaptation process 700, both of which are suitable for use with a portable medical device that is configured as described here. The various tasks performed in connection with a described process may be performed by software, hardware, firmware, or any combination thereof. For illustrative purposes, the following description of these processes may refer to elements mentioned above in connection with FIGS. 1-9. In practice, portions of a described process may be performed by different elements of the medical device, e.g., a situational awareness sensor, a functional module (such as the decision module), a processing element or component, or the like. It should be appreciated that a described process may include any number of additional or alternative tasks, the illustrated tasks need not be performed in the illustrated order, and a described process may be incorporated into a more comprehensive procedure or process having additional functionality not described in detail herein. Furthermore, an embodiment might omit one or more of the illustrated tasks, as long as the intended functionality is not adversely affected.

Referring to FIG. 10, the intelligent alerting process 600 assumes that the electronic device is configured to support the intelligent alerting and alarm methodologies described above. In this regard, the process 600 monitors the operation of the medical device in an appropriate manner (task 602) for the occurrence of an alert, alarm, reminder, or notification condition. If the process 600 detects an alert condition associated with the operation of the device (query task 604), then it can proceed to the next task. Otherwise, the process 600 can continue monitoring (task 602) the operation of the device. In response to the detected alert condition, the process can perform an appropriate scanning operation with one or more situational awareness sensors (task 606) that are onboard the host device. In certain embodiments, a plurality of situational awareness sensors are used to obtain respective sensor data that is indicative of current conditions (operating conditions, environmental conditions, physical status, geographic location, etc.) associated with the host device.

The scanning operation need not be initiated until an alert condition has been detected (in other words, task 606 is performed after query task 604 detects the alert condition). Initiating the scanning operation in this manner may be desirable to save power and processing resources. Otherwise, continuous or scheduled background scans could be implemented. The collected sensor data is used as input(s) to a decision module resident at the host device (task 608). As mentioned previously, the decision module might include or maintain a suitable decision tree, a lookup table, a decision algorithm, or a decision function that processes or analyzes the collected sensor data. The process 600 uses the collected sensor data to determine, select, or identify a preferred alerting scheme from a plurality of different available alerting schemes (task 610). In certain embodiments, task 610 is executed by traversing a decision tree using the collected sensor data. After traversing the decision tree, the preferred alerting scheme for the detected alert condition can be identified. In this manner, the preferred alerting scheme will be influenced by the present conditions, state, and status as interrogated by the medical device.

Once the preferred alerting scheme has been identified, the process 600 can generate an alert (or a sequence of alerts) in accordance with the preferred alerting scheme (task 612). As mentioned above, task 612 may be associated with the generation of any number of different alert notification types, using any number of alert generating elements. If the process 600 determines that the alert has been disabled (query task 614) by the user or otherwise, then it can silence or deactivate the alert generating element(s) and continue as needed. For example, the process 600 might be re-entered at task 602 to continue monitoring for another alert condition.

Adaptation of Decision Module

Referring now to FIG. 11, the alerting scheme adaptation process 700 assumes that the electronic device is configured to support the intelligent alerting and alarm methodologies described above. In this regard, the process 700 can maintain a suitable decision algorithm, decision tree, decision logic, and/or intelligence that selects alerting schemes for the host device (task 702). If the process 700 detects an alert condition (query task 704), then it can proceed and generate one or more alerts in accordance with the preferred alerting scheme selected by the decision intelligence (task 706).

For this embodiment, the process 700 obtains and/or records information that is associated with user reactions to the alert (task 708). For example, the host device could keep track of user responses, reaction times, and/or user inputs related to a given alert condition. Thus, the process 700 can determine whether or not the selected alerting scheme was effective and efficient at notifying the user, whether or not the selected alerting scheme was overridden or quickly disabled by the user, whether the selected alerting scheme went ignored by the user, etc. Moreover, the process 700 can dynamically adapt, update, alter, or modify the decision algorithm, tree, logic, and/or intelligence (if so desired) in response to the obtained user reaction information (task 710). Such adaptation allows the decision module of the device to evolve, train itself, and learn the habits and preferences of the user. Consequently, the decision making processes of the host device can be optimized in an ongoing manner to produce better and more effective results.

In certain embodiments, the process 700 might alter the decision logic only after a predetermined number of iterations have been performed to contemplate actual response trends rather than individual responses. In practice, the host device could leverage any number of techniques, methodologies, or protocols to adapt its decision logic. For example, task 710 might leverage one or more of the following technologies, without limitation: artificial intelligence; evolutionary computing; expert systems; neural networks; or the like. Moreover, the process 700 might stabilize after continued use by the same person, such that the decision module becomes "fixed" or is rarely updated in an ongoing manner. In other words, after some training or learning period, the settings of the decision module might reflect the best decision logic for all of the alert conditions monitored by the host device.

EXAMPLES

An electronic device with onboard situational awareness sensors could be used to determine a vast number of different environmental conditions and respond accordingly. For instance, optical sensors on all sides of the device could be used to determine the amount of light, whether the light is natural or artificial, and, therefore, whether the device is indoors or outdoors. Proximity sensors could be used to determine if the device is in the open, in a pocket, in a purse, etc. Temperature sensors could be used to determine if the device is being held by the user or whether the device is in close contact with the body on any side. Motions sensors could be used to determine if the device is sitting on a table (or if the user is walking with the device). A gyroscope could be used to determine which way is up, down, or sideways. Sound sensors could be used to check the ambient noise levels near the device. Force or pressure sensors could be used to check whether the device is covered, in the open, or whether the user is sitting or sleeping on it.

By traversing a decision tree, by process of elimination, or by using a decision algorithm, the device can attempt to resolve the current operating condition and environment of the device, and generate appropriate alert notifications that are suitable for the current state of the device. For example, the device might first alert the user with a gentle vibrating alert. This can be repeated at relatively long intervals at the outset. If the user does not respond to the gentle vibrations, the device might switch the vibration mode to something out of the ordinary (such as a more aggressive vibration or rattling). If the user still does not respond, the device could use the ambient noise measurement to adjust and play an audio alarm. This audible alert could also be correlated to the internal clock and ambient lighting readings to determine if the user might be sleeping, at work, etc. If the device determines that the user should be responsive (e.g., the alert condition was detected during normal waking hours), then it can increase the alert volume and/or change the alert tone based on physical proximity readings.

For instance, if the user is in a conference room during a meeting and the device is in a pocket, then the device might detect low ambient light, an object (the pocket material) within close proximity, and low ambient noise. Consequently, the next alert escalation might be a low-pitched tone of moderate intensity, since high-pitched tones would probably be filtered by the fabric of the pocket. As a second example, if the user is at the movies and can't access the device quickly, a pressure or force sensor could be used to allow the user to disable the alert by squeezing the device. As a third example, if the device is left on a hard surface, such as a nightstand or a table, could switch to a high-pitched short tone. The device could determine this status by detecting an object on one side, ambient light on the other sides, and no significant heat sources on any side. As yet another example, if the device determines that the user might be sleeping (by reading low ambient lighting, a fairly quiet environment, and a corresponding time of day), then it could slowly ramp up the alert sound level or tone so that the alert does not startle the user.

Certain embodiments could use such a graduated response that culminates in the device employing most or all of its alert generating elements if no user response is detected after a specified period of time. Other measures may also be taken if no user response is detected, e.g., automatically calling 911 or an emergency response number, automatically generating a text message to a designated contact, generating an emergency display message, etc.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method of operating a portable medical device that includes at least one onboard situational awareness sensor, the method comprising:

maintaining a decision algorithm that selects alerting schemes for a hand-held portable insulin infusion device, wherein the decision algorithm processes sensor data obtained by the at least one onboard situational awareness sensor to select preferred alerting schemes for alert conditions of the hand-held portable insulin infusion device, the alert conditions including an indication of a blood glucose level and the at least one onboard situational awareness sensor obtains sensor data indicative of a load on an exterior housing of the hand-held portable insulin infusion device and obtains sensor data indicative of a wavelength for ambient light near an exterior housing of the portable insulin infusion device;

generating alerts in accordance with preferred alerting schemes selected by the decision algorithm;

obtaining information associated with user reactions to the alerts, resulting in obtained user reaction information; and dynamically adapting the decision algorithm in response to the obtained user reaction information, wherein:

the preferred alerting scheme calls for a first alert notification type when the load data indicates higher loading on the exterior housing of the hand-held portable insulin infusion device or the wavelength data indicates artificial ambient light near the exterior housing of the electronic device; and the preferred alerting scheme calls for a second alert notification type when the load data indicates lower loading on the exterior housing of the hand-held portable insulin infusion device or the wavelength data indicates natural ambient light near the exterior housing of the electronic device.

2. The method of claim 1, wherein generating alerts comprises annunciating an audible alert having audible characteristics determined by the preferred alerting scheme.

3. The method of claim 1, wherein generating alerts comprises displaying an alert message having content determined by the preferred alerting scheme.

4. The method of claim 1, wherein generating alerts comprises generating a visible alert having visual characteristics determined by the preferred alerting scheme.

5. The method of claim 1 wherein generating alerts comprises generating a physical feedback alert having haptic characteristics determined by the preferred alerting scheme.

6. The method of claim 1 wherein generating alerts comprises generating a combined alert having at least two of the following characteristics: audible, visual, textual, and haptic.

7. The method of claim 1 wherein using the at least one onboard situational awareness sensor to obtain the sensor data occurs after detecting the alert condition.

8. The method of claim 1 wherein generating alerts comprises escalating an alert notification in a manner defined by the preferred alerting scheme.

9. The method of claim 1 wherein:
the at least one onboard situational awareness sensor comprises a sound sensor that obtains ambient sound data indicative of sound level near the electronic device;
the preferred alerting scheme calls for the first alert notification type when the ambient sound data indicates higher sound levels near the electronic device; and
the preferred alerting scheme calls for the second alert notification type when the ambient sound data indicates lower sound levels near the electronic device.

10. The method of claim 1 wherein:
the at least one onboard situational awareness sensor comprises a physical proximity sensor that obtains proximity data indicative of the proximity of objects near the electronic device;
the preferred alerting scheme calls for the first alert notification type when the proximity data indicates longer distances relative to the electronic device; and
the preferred alerting scheme calls for the second alert notification type when the proximity data indicates shorter distances relative to the electronic device.

11. The method of claim 1 wherein:
the at least one onboard situational awareness sensor comprises a light intensity sensor that obtains intensity data indicative of ambient light intensity near the electronic device;
the preferred alerting scheme calls for the first alert notification type when the intensity data indicates higher ambient light intensity near the electronic device; and
the preferred alerting scheme calls for the second alert notification type when the intensity data indicates lower ambient light intensity near the electronic device.

12. The method of claim 1 wherein:
the at least one onboard situational awareness sensor comprises a geographic positioning sensor that obtains position data indicative of present geographic position of the electronic device; and
the preferred alerting scheme calls for different alert notification types based upon the position data.

13. The method of claim 1 wherein:
the at least one onboard situational awareness sensor comprises a clock that obtains time data for the electronic device; and
the preferred alerting scheme calls for different alert notification types based upon the time data.

14. The method of claim 1 wherein:
the at least one onboard situational awareness sensor comprises a calendar that obtains calendar data for the electronic device; and
the preferred alerting scheme calls for different alert notification types based upon the calendar data.

15. The method of claim 1 wherein selecting the alerting schemes comprises:
traversing a decision tree using the collected sensor data; and
identifying the preferred alerting scheme after traversing the decision tree.

16. The method of claim 1, wherein:
the preferred alerting scheme calls for a sequence of different alert notification types; and
generating the alert generates the sequence of different alert notification types until the alert is disabled by a user.

17. The method of claim 1, wherein:
the preferred alerting scheme calls for escalation of the alert; and
generating the alert escalates at least one characteristic of the first alert notification type or second alert notification type until the alert is disabled by a user.

* * * * *